(12) United States Patent
Levin et al.

(10) Patent No.: US 9,265,451 B2
(45) Date of Patent: Feb. 23, 2016

(54) METHOD AND APPARATUS FOR DETERMINING SPASTICITY

(76) Inventors: Mindy Levin, Montreal (CA); Anatol Feldman, Montreal (CA); Eric Johnstone, Montreal (CA)

( * ) Notice: Subject to any disclaimer, the term of this patent is extended or adjusted under 35 U.S.C. 154(b) by 2315 days.

(21) Appl. No.: 11/910,251

(22) PCT Filed: Mar. 31, 2006

(86) PCT No.: PCT/CA2006/000489
§ 371 (c)(1),
(2), (4) Date: Nov. 27, 2007

(87) PCT Pub. No.: WO2006/102764
PCT Pub. Date: Oct. 5, 2006

(65) Prior Publication Data
US 2008/0312549 A1 Dec. 18, 2008

Related U.S. Application Data

(60) Provisional application No. 60/666,572, filed on Mar. 31, 2005.

(51) Int. Cl.
*A61B 5/04* (2006.01)
*A61B 5/11* (2006.01)
*A61B 5/0488* (2006.01)
*A61B 5/00* (2006.01)

(52) U.S. Cl.
CPC ............ *A61B 5/1121* (2013.01); *A61B 5/0488* (2013.01); *A61B 5/1124* (2013.01); *A61B 5/4519* (2013.01); *A61B 5/4058* (2013.01); *A61B 5/4528* (2013.01)

(58) Field of Classification Search
CPC ..................................................... A61B 5/1121
USPC ............ 600/546, 587, 595, 372, 553; 601/27; 128/897
See application file for complete search history.

(56) References Cited

U.S. PATENT DOCUMENTS

| | | | |
|---|---|---|---|
| 4,971,069 A | 11/1990 | Gracovetsky | |
| 5,052,406 A | 10/1991 | Nashner | |
| 5,474,088 A * | 12/1995 | Zaharkin et al. | 600/595 |
| 6,063,044 A * | 5/2000 | Leonard et al. | 600/587 |
| 6,589,190 B2 * | 7/2003 | Kanderian et al. | 600/587 |

OTHER PUBLICATIONS

Jobin et al., Regulation of Stretch Reflex Threshold in Elbow Flexors in Children with Cerebral Palsy: A New Measure of Spasticity, 2000, Developmental Medicine & Child Neurology, 42, 531-540.*
Levin et al., Deficits in the Coordination of Agonist and Antagonist Muscles in Stroke Patients: Implications for Normal Motor Control, 2000, Brain Research, 352-369.*

(Continued)

*Primary Examiner* — Brian Szmal
(74) *Attorney, Agent, or Firm* — Anglehart et al.

(57) ABSTRACT

There is provided a system and a method for quantitative measurement of spasticity in a patient. It has been found that stretch reflex measurements, that are quantitatively indicative of spasticity, can be obtained by recording an EMG signal while the limb is being moved at a variety of angular velocities. The method advantageously allows the clinician to perform the test at the bedside by eliminating the need for cumbersome mechanical components for moving the limb while providing quantitative measurements.

1 Claim, 4 Drawing Sheets

(56) References Cited

OTHER PUBLICATIONS

Andra Calota et al., Spasticity measurement based on tonic stretch reflex threshold in stroke using a portable device, 2008, Clinical Neurophysiology, 119(2008), 2329-2337.

Andra Calota et al., Tonic Stretch Reflex Threshold as a Measure of Spasticity: Implications for Clinical Practice, Topics in Stroke Rehabilitation, vol. 16, 2009, 177-188.

Canada application 2643477 Office action dated Jun. 6, 2013 with related claims 1-25.

Mindy F. Levin et al., The role of stretch reflex threshold regulation in normal and impaired motor control, Brain Research, vol. 657, Issues 1-2, Sep. 19, 1994, pp. 23-30.

Mullick AA et al., Stretch reflex spatial threshold measure discriminates between spasticity and rigidity, Clinical Neurophysiology, 124 (2013) 740-751.

Musampa NK et al., Relationship between stretch reflex thresholds and voluntary arm muscle activation in patients with spasticity, Exp Brain Res. Aug. 2007;181(4):579-593. Epub May 3, 2007.

* cited by examiner

METHOD AND APPARATUS FOR DETERMINING SPASTICITY

FIELD OF THE INVENTION

This invention relates to the field of muscle activity assessment and more specifically to the assessment of spasticity in muscles.

BACKGROUND OF THE INVENTION

Spasticity is a neurological symptom affecting children and adults causing an abnormal increase in muscle tone that occurs when the affected muscle is stretched. Spasticity can occur in neurological disorders that damage the parts of the brain and the nervous system that control voluntary movements. The most common disorders leading to spasticity are cerebral palsy, spinal cord injury, multiple sclerosis, stroke, and traumatic brain injuries, due to a lack of oxygen, physical trauma, haemorrhage, or infection. Some of these injuries can occur at birth and others can occur during adulthood.

The severity of spasticity can range from slight muscle stiffness to deformity and permanent muscle shortening, called contracture. Spasticity often interferes with voluntary movement and with the proper positioning of the body. The presence of spasticity interferes with the accomplishment of activities of daily living such as dressing, eating, and grooming. Spasticity also interferes with mobility, seating and transfers such as moving from the bed to the wheelchair or from sitting to standing. Spasticity also may make it difficult to sit comfortably, or to change positions frequently enough to prevent joint pain and pressure sores. Spasticity in the feet can prevent comfortable fitting of shoes. Severe spasticity may cause painful joint misalignments and limitations in joint movement interfering with hygiene.

Physical, pharmacological and surgical therapies are aimed at decreasing spasticity and restoring motor control. Physical treatments include stretching and positioning to prevent the development of muscle contractures. Pharmacological approaches include oral or intrathecal delivery of drugs targeting the neuromuscular junction of the muscle or the synaptic pathways and nerves innervating the muscle. Local injections of drugs that weaken or paralyze overactive muscle (chemodenervation agents) can be effective for spasticity in isolated muscles. Severe spasticity that cannot be effectively treated with drugs or injections may respond to surgical destruction of some overactive nerves in the spine. Contracture may be treated with serial casting to allow tendons to stretch, or orthopedic surgery if required.

A major problem in the treatment of spasticity is that a sensitive measure of the phenomenon that can be applied at the bedside or in the clinic to make treatment decisions and to judge the effectiveness of treatment does not yet exist. Until now, a variety of different clinical measures have been used to assess spasticity. The current 'gold standard' is a 5 point scale (Ashworth Scale) that can only distinguish the presence or absence of spasticity but is not sensitive to its severity. What is more, the scale is subjective, so that the evaluator must 'judge' how much resistance is felt when he or she stretches the muscle. Clinicians and researchers agree that this measure is inadequate since it does not discriminate between different types of hypertonicity and does not adequately reflect the severity of spasticity. Furthermore while apparatuses exist for obtaining spasticity measurements that use mechanical components to apply a torque to a joint, they are cumbersome and difficult to adapt to the various types of joints and may create discomfort in the patient.

The identification of the need to have a better (more sensitive and discriminative) measure of spasticity that is easily accessible to the clinician has been apparent for many years.

SUMMARY OF THE INVENTION

There is provided a system and a method for quantitative measurement of spasticity in a patient. It has been found that stretch reflex measurements, that are quantitatively indicative of spasticity, can be obtained by recording an EMG signal while the limb is being moved at a variety of angular velocities. Each movement of the limb from an initial to a final position need not be performed at constant velocity and therefore the method advantageously allows the clinician to perform the test at the bedside by eliminating the need for cumbersome mechanical components for moving the limb while providing quantitative measurements.

Thus, there in one aspect of the invention there is provided a method for providing a quantitative measure of spasticity in a limb, comprising providing measurement apparatus for measuring a joint angle and EMG activity in the limb, determining a threshold EMG activity value in the limb, determining a zero angle defining an initial position of the limb, imparting a movement to the limb from the initial to a final position while measuring an EMG activity value in muscles of the limb and angles and velocities at which the limb is moved, recording angle and velocity as a data point at which the measured EMG value crosses the threshold EMG activity value, repeating the movement at a range of velocities until a set of data points are acquired and recorded, and processing the set of data points and computing a threshold angle value and a sensitivity of the threshold angle to velocity value, the values providing a quantitative measure of spasticity in the limb.

In another aspect there is also provided a system for providing a quantitative measure of spasticity in a limb, the system comprising, a joint angle sensor capable of detecting angular motion in the limb, an angular velocity determinator, an EMG detector for measuring stretch reflex activity in the limb, an EMG signal threshold determinator for determining onset of stretch reflex activity, a zero set to record a zero angle, a stretch reflex detector for recording velocity and angle data at onset of stretch reflex activity, spasticity evaluator module to process the angle and velocity data recorded at onset of stretch reflex activity and provide a measure of spasticity, acquisition control/user feedback allowing a clinician to activate settings and for guiding the clinician in a choice of a range of velocities for data acquisition; and a data quality evaluator for evaluating a quality of the measure of spasticity provided by the spasticity evaluator module and generating a signal to the acquisition control/user feedback that is reflective of the quality.

DETAILED DESCRIPTION OF THE INVENTION

Figure 1:
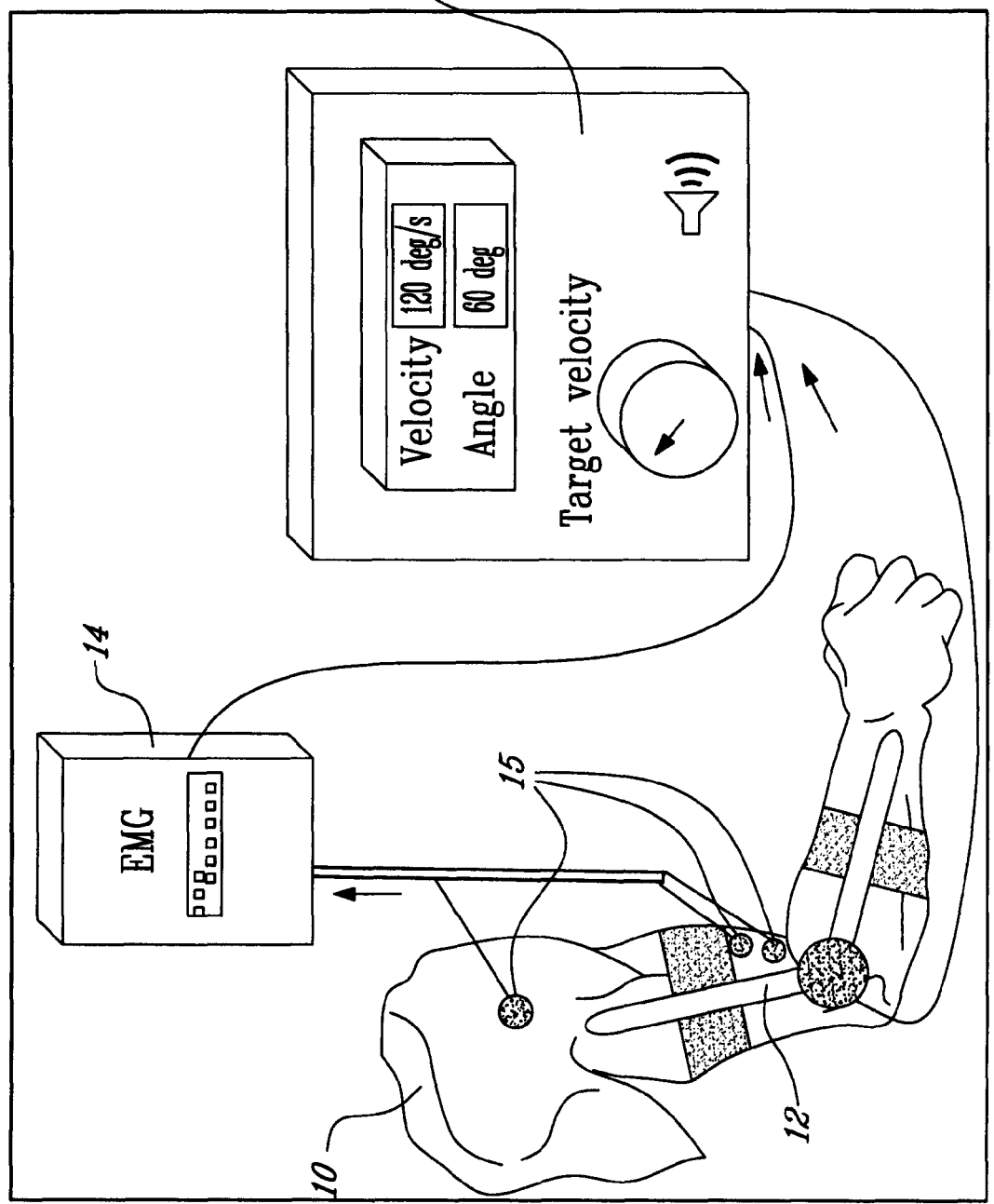
FIG. 1 is a schematic representation of an embodiment of the apparatus of the invention for determination of spasticity.

There is provided a method and apparatus that advantageously measures spasticity in an objective and reproducible way. Referring to FIG. 1 a schematic diagram of spasticity measurements being performed on a limb according to an embodiment of the method of the present invention is shown. The set up allows the acquisition of EMG signals, joint angles $\Theta$ and angular velocities $\omega$ data that are used to provide a quantitative measurement of spasticity. In FIG. 1 an arm 10 is shown in which the elbow (the joint) is bent at an angle $\Theta$. A joint angle sensing device such as a goniometer 12 is attached to the arm to provide angle measurements and muscle activity is monitored by an EMG 14 comprising electrodes 15. The data is processed by data processor 16 to assess spasticity by computing the angle $\lambda$ at which the onset of the stretch reflex (SR) is triggered. The results may be compared to results obtained for normal individuals or individuals with similar or different diseases.

Figure 2:
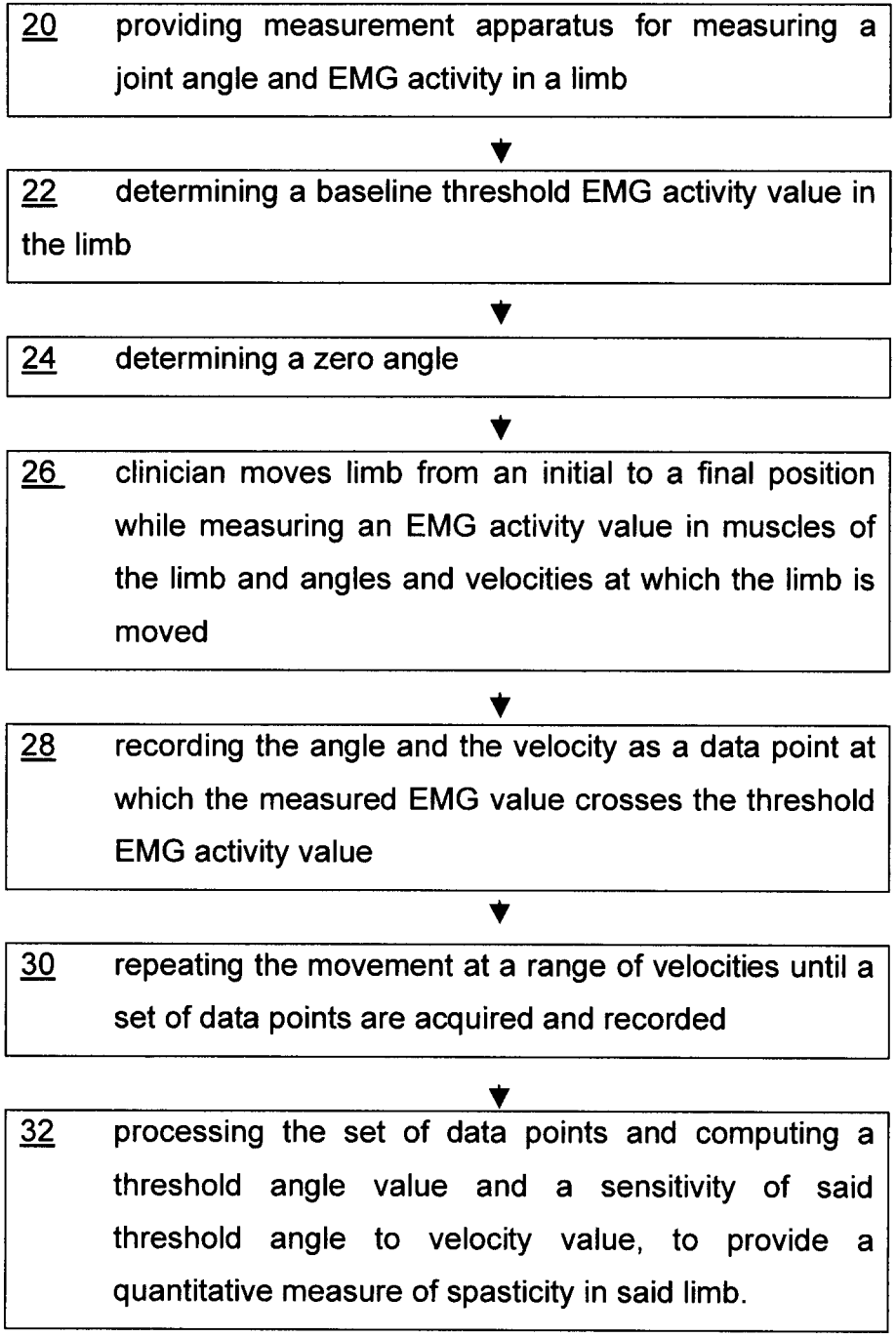
FIG. 2 is flow chart of an embodiment of the method for determination of spasticity.

In one embodiment, and referring to FIG. 2, the method of the present invention comprises providing at 20 means for sensing angles of a moving joint. At 22 a threshold EMG activity value is determined in the limb that corresponds to the onset of the SR activity. This threshold can be determined by the clinician in a measurement session by acquiring a plurality of EMG while the joint is being flexed/stretched. The threshold generally corresponds to the angle at which an EMG signal value rises above a value considered to be statistically different from the baseline. Next an angle (zero angle) at which no EMG activity is detected (rest position) is determined at 24. Measurement angles $\Theta$ are defined relative to the zero angle. It will be appreciated that the zero angle may vary from patient to patient and that it may correspond to either the "open" or "closed" position of the joint. Assessment of spasticity is based on the static stretch reflex threshold (SRT) which is the joint angle at which the muscle start to be activated. While this angle can be determined using a "static" approach (by quasi-statically stretching the muscles), it is preferred to determine the SRT using a dynamic approach in which the limb is moved and the angular velocity of the joint is recorded as a function of the angle. For each velocity of stretch, the angle at which the onset of SR is detected is recorded and a regression is performed to obtain the static SRT angle at velocity zero. Thus, referring back to FIG. 2, the clinician performs, at 26 and 30, a series of flexions/extensions of the joint at a plurality of velocities while the EMG activity, the angle and the angular velocity are measured. For each flexion/extension, the angle and the velocity at which the EMG threshold is crossed are recorded at 28 and the data are processed at 32 to determine SRT and assess spasticity. It will also be appreciated that an upper and a lower angular limit may be determined which may serve as a basis, together with the SRT angle, to assess spasticity.

It was found that the velocity at which the limb is moved from an initial to a final position need not be constant thereby allowing a clinician to impart the motion to the limb and eliminating the need for a controlled motorized motion of the limb. However, it will be appreciated that a simple motorized limb flexor that does not necessarily comprise elaborated velocity controlling elements, which would therefore be better suited for easy and convenient bedside measurements, may also be used.

During the procedure, feedback is preferably provided to the clinician by, for example, displaying the EMG traces, the angles, the angular velocity and SRT results. Such feedback allows the clinician to properly adjust the baseline EMG threshold and the zero angle prior to beginning the measurement and to assess the quality of data acquisition during or after measurement. Feedback can also be provided to the clinician to prompt him or her to acquire additional measurements at angular velocities different from those already recorded to minimize the error on the determination of SRT.

The SRT can be determined by interpolating the data using the SR threshold at each velocity so as to obtain the SR angle at zero velocity. The data can be fitted using a regression analysis as would be known to those skilled in the art. The equation characterizing the line is:

$$\Theta + \mu\omega - \lambda = 0$$

wherein $\omega = d\Theta/dt$, and $\mu$ is the sensitivity of the threshold $\lambda$ to velocity. The sensitivity $\mu$ and threshold $\lambda$ are used to characterize the level of spasticity. The results surprisingly showed that the method is robust with regard to variations in the velocity at which the limb is moved. That is to say, the velocity need not be constant during a flexion/extension acquisition therefore making it possible for a clinician to move the limb as opposed to using a mechanically controlled apparatus to apply a torque to the limb. This advantageously allows the measurements to be performed at bedside in a minimum amount of time.

Figure 3A:
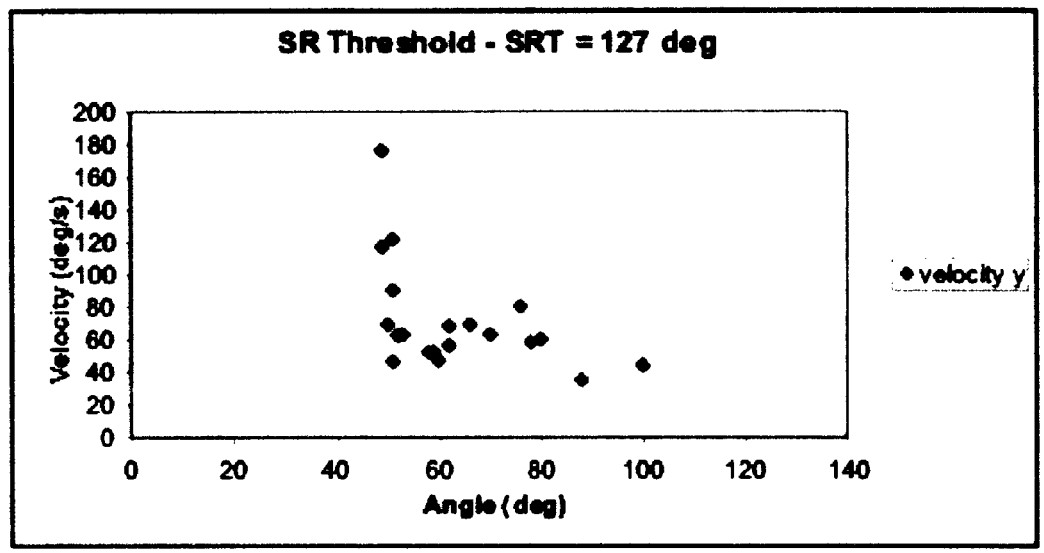
FIGS. 3A and B are graphs showing results of stretch reflex thresholds determined in one patient at two different times.
Figure 3B:
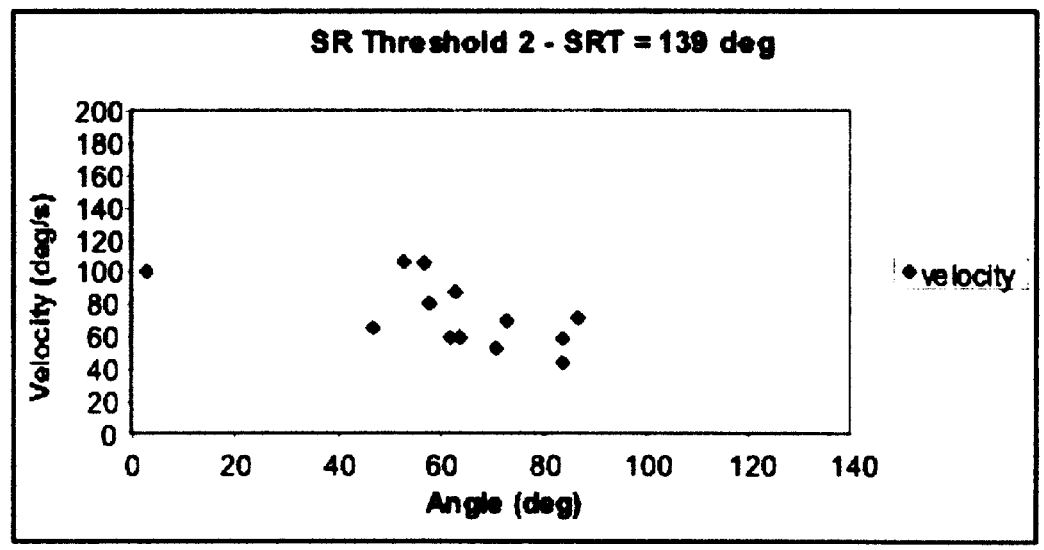

Referring to FIG. 3, an example of angle-velocity curves measured with an embodiment of the device of the present invention is shown. The graphs show results of two measurement sessions performed on the same patient by the same therapist at two different times. The patient is a 69 year old male patient who had a stroke resulting in left-sided paresis, 2 years ago. The computed stretch reflex thresholds were 127 deg and 139 deg in this test-retest.

In another aspect of the invention, there is provided a system for obtaining spasticity measurements which comprises a joint angle sensor capable of detecting angular motion in said limb, an angular velocity determinator, an EMG detector for measuring stretch reflex activity in the limb, an EMG signal threshold determinator for determining onset of stretch reflex activity, a zero set to record a zero angle, a stretch reflex detector for recording velocity and angle data at onset of stretch reflex activity, spasticity evaluator module to process said angle and velocity data recorded at onset of stretch reflex activity and provide a measure of spasticity, a data quality evaluator; and an acquisition control/user feedback module allowing a clinician to activate settings and for guiding the clinician in a choice of a range of velocities for data acquisition. Spasticity can also be expressed as a function of $\lambda$ and the biomechanical range of the joint angle.

Figure 4:
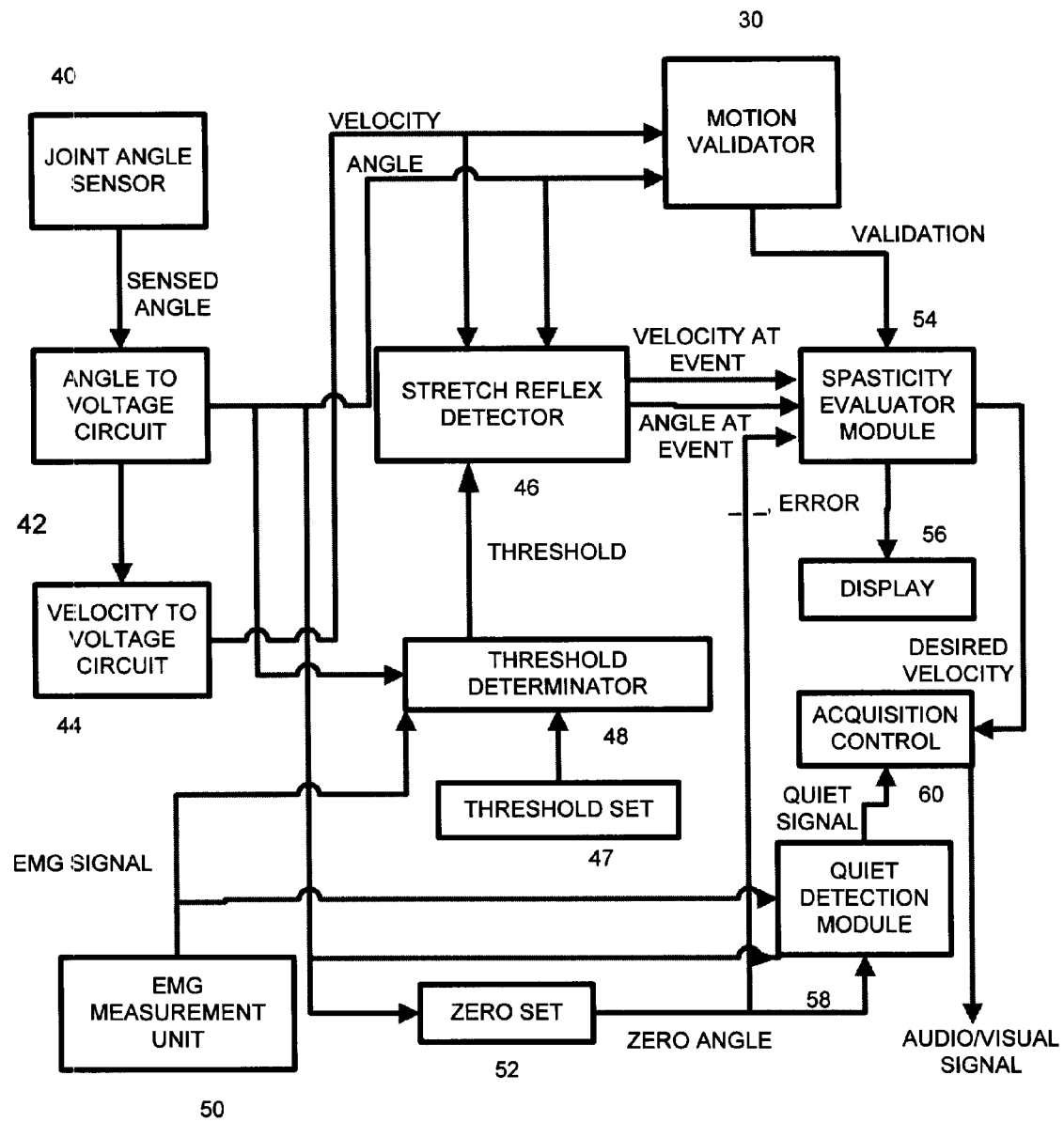
FIG. 4 is a diagram of an embodiment of the system of the present invention.

An embodiment of the system is shown in FIG. 4. The system comprises a joint angle sensor 40 which allows the detection of the joint angle as a function of time from which the velocity can be derived. The sensed angle and the derived velocity are converted to electrical signals by angle to voltage 42 and velocity to voltage 44 circuits which provide input data to the stretch reflex detector 46. The angle also serve as input data to the threshold determinator 48 which also receives input data from EMG measurement unit 50. The threshold determinator 48 establishes the threshold that defines the onset of stretch reflex activity that is subsequently used to detect a spasticity event. The angle data is also fed into the zero set unit 52 that records the clinician determined zero angle defined above. Stretch reflex detector outputs the velocity and the angle detected at or just before detection of the stretch reflex signal which occurs when the threshold is crossed. The velocity and angle data at the onset of the stretch reflex event are fed into spasticity evaluator module 54 which also receives the position for the zero angle as input data. Spasticity evaluator 54 can then perform the necessary data processing for determining $\lambda$ and $\mu$ (angle of SRT and sensitivity) that are indicative of the degree of spasticity. The results can be displayed on display 56. It will be appreciated that display 56 can also display EMG traces, angle measurements, velocity data and the like to provide feedback to the clinician.

A quiet detection module 58 is provided that processes data from the zero set 52, EMG measurement unit 50 and angle to voltage circuit 44 to determine when the limb is in an appropriate starting position. For example, the starting position could be defined by the angle $\Theta$ being within ±10 degrees of the zero angle and by the EMG being quiet for a certain amount of time, for example 5 seconds. It will be appreciated that other starting conditions could be defined depending on the joint, disease and other factors as would be obvious to one skilled in the art. The quiet detection module generates a quiet signal that is forwarded to the acquisition control/user feedback module 60 which in turn can generate a signal, such as an audio signal, to alert the clinician that measurements can be started. Acquisition control/user feedback module 60 may also generate other signals to guide the clinician in the acquisition of data. For example, the clinician could be prompted to acquire additional data for the spasticity evaluator module 54 to improve spasticity assessment. Thus a data quality evaluator can be provided that can analyze, for example by performing a statistical analysis, the measured spasticity value and send a signal to the acquisition control/user feedback module that will encode necessary information to prompt the user to acquire additional signal. The user may, based on the signal, adjust the speed at which the limb is moved, modify the zero angle and the like. The actual velocity may be recorded whether or not it corresponds to the requested velocity. For example a glissando (sweep) audio signal can be generated to indicate at which velocity the limb should be moved. Alternatively a visual signal such as an animation showing the movement so that the clinician can adjust the speed to match that of the animation. The animation can be repeated at intervals to allow the clinician to adjust by repeating the motion several times. The acquisition control/user feedback module may comprise a foot pedal enabling the user/clinician to activate settings, such as recording the threshold and the zero angle, using his/her foot thereby freeing his/her hands to manipulate the limb.

Additional options and features of the system are now described. They are intended to be exemplary and do not limit the scope of the invention.

Optionally the system may comprise a motion validator 30 to validate angle and velocity measurements and accept/reject data based on predetermined criteria or ranges for these data. For example it may be desirable to move the limb within a range of velocities. Thus the motion validator can reject measurements if the variation in the velocity imparted to the limb falls outside a predetermined range.

The system can operate in real time to provide instant feedback to the clinician. However it will be appreciated that the system can be computerized to allow storage and later retrieval/processing of the data.

The joint angle can be measured by a goniometer or by a motion capture system, for example. The goniometer sensing could be by potentiometer, optical encoder, or bend sensor. Furthermore, the output of the joint angle sensor could be a voltage, a series of pulses from an incremental optical encoder, or a parallel output from an absolute optical encoder. The angle information can be sent to the computer input via a wire or via a radio signal such as Bluetooth or ZigBee.

The angular velocity can be obtained by analog differentiation of the voltage signal from a potentiometric goniometer. If the goniometer uses an incremental optical encoder the velocity can be measured as the reciprocal of the time between successive pulses. Similarly, if an absolute encoder is used, the velocity could be measured as the reciprocal of the time between changes in absolute output.

When measuring individuals with spasticity, false readings may be obtained due to limb positioning or the voluntary movements made by the individual. Some of these signals can be determined to be incorrect algorithmically by the motion validator 62, and hence ignored by the program. The examiner can also remove incorrect data points immediately after they occur by pressing a foot switch, or later when the data set is presented. Some of these false data points will be displayed as outliers that can also be removed algorithmically.

As mentioned above, the data required by the spasticity evaluator module are the velocity and angle. Preferably these data are those acquired 30 ms before the EMG event. Therefore, a memory of the movement extending back at least 30 ms should preferably be maintained. In fact, the complete acquisition from start to end is preferably retained. That is, the velocity, angle, and complete EMG waveform are available to the clinician and can be viewed in various ways as overlaid graphs, for example.

The threshold is set by adjusting the amplitude of the EMG signal so that the response of the spastic muscle is greater than a fixed reference value. This level setting can be done by a potentiometer or by a variable gain amplifier. The gain of the amplifier could be set algorithmically during the set-up. The foot switch may be used to indicate to the program that the EMG threshold should be set during the subsequent movements.

The threshold level is a fixed level. When the EMG signal exceeds the reference level, the threshold signal is generated. The reference can be exceeded on either the positive or negative excursion of the EMG signal. This can be detected digitally by ignoring the most significant bit (msb) of the digitized EMG signal. (If the EMG is assumed to be converted to a signed integer, the sign is determined by the msb) If the threshold is measured in an analog circuit before acquisition, the EMG signal can be full-wave-rectified before going to the threshold determinator.

The EMG signal is generated by placing electrodes on the patient. The electrodes are placed on a specific muscle so that consistent measurements are made between and among patients. Holding and moving the limb should also be done consistently for all patients. An EMG Measuring Unit is typically an instrumentation amplifier with low-pass and high-pass filtering. The low-pass filter removes frequencies above one half of the sampling frequency of the data acquisition device to avoid aliased signals. The high-pass filter removes motion artifacts, which are electrical signals generated by movement of the electrodes on the skin or by movement of the wires (if present).

A predetermined minimum number of data points should be collected to generate a meaningful result. After collecting the minimal data set, the program performs a linear regression as each new data point is collected. When the confidence interval is below some predetermined size, the program reports that it has found the spastic deficit. The program could also examine the data set to ignore outliers.

The display can be a ¼ VGA screen, such as an LCD type. The display can be used to display instruction manual, tutorials, correct placement of electrodes and goniometer, movies showing an examiner performing the movements, and display of results.

The device is designed to measure the severity of spasticity. It can potentially be used to measure spasticity at the wrist, elbow, shoulder, ankle, knee and hip. It can be used in the research laboratory, at a patient's bedside in the hospital ward, in a medical clinic, in a rehabilitation center or in a patient's home. Patients in whom the measurement of spasticity is needed include but is not limited to children and adults with cerebral palsy or other congenital diseases, adults with stroke, brain injury, multiple sclerosis, amylotrophic lateral sclerosis, spinal cord injury, and other neuromuscular disorders. Measurement of the stretch reflex threshold can be used to quantify spasticity and to monitor patient progress following the administration of physical, pharmacological or surgical treatments to reduce spasticity and to improve motor control.

The device may be used by physiotherapists, occupational therapists, nurse practitioners, medical doctors (neurologists, orthpaedists, surgeons) and researchers. It will be appreciated that such persons skilled in the art would be capable of operating the device of the invention including selecting appropriate muscles for placing electrodes for EMG recordal.

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

The invention claimed is:

1. A method of patient care to reduce spasticity and/or improve motor control of a limb, the method comprising:
   a) providing measurement apparatus for measuring a joint angle and EMG activity in said limb;
   b) determining a threshold EMG activity value in said limb;
   c) determining a zero angle defining an initial position of said limb;
   d) imparting a movement to said limb by a clinician from said initial to a final position while measuring an EMG activity value in muscles of said limb and angles and velocities at which said limb is moved;
   e) recording angle relative to said zero angle and velocity as a data point at which said measured EMG value crosses said threshold EMG activity value to determine a threshold angle at said velocity;
   f) repeating said movement at a range of velocities until a set of data points are acquired and recorded to provide a relationship between velocities and threshold angles;
   g) algorithmically validating said data points based on said relationship between velocities and threshold angles;
   h) repeating one of step b), c), d), e), f) or combination thereof if said data points are outside predetermined quality criteria to obtain a set of valid data points;
   i) computing a stretch reflex threshold value and a sensitivity of said threshold value to velocities value using said valid data points;
   j) outputting said stretch reflex threshold value and said sensitivity of said threshold angles to velocities value to provide a quantitative measure of spasticity in said limb; and
   treating a patient with a physical, pharmacological or surgical treatment based on said quantitative measure.

* * * * *